United States Patent
Meral et al.

(10) Patent No.: US 11,337,673 B2
(45) Date of Patent: May 24, 2022

(54) USING REFLECTED SHEAR WAVES FOR MONITORING LESION GROWTH IN THERMAL ABLATIONS

(71) Applicant: KONINKLIJKE PHILIPS N.V., Eindhoven (NL)

(72) Inventors: Faik Can Meral, Mansfield, MA (US); Shriram Sethuraman, Lexington, MA (US); Pingkun Yan, Gaithersburg, MD (US); William Tao Shi, Wakefield, MA (US); Jochen Kruecker, Andover, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 287 days.

(21) Appl. No.: 16/306,938

(22) PCT Filed: Jun. 5, 2017

(86) PCT No.: PCT/EP2017/063598
§ 371 (c)(1),
(2) Date: Dec. 4, 2018

(87) PCT Pub. No.: WO2017/211757
PCT Pub. Date: Dec. 14, 2017

(65) Prior Publication Data
US 2019/0142366 A1 May 16, 2019

Related U.S. Application Data

(60) Provisional application No. 62/348,302, filed on Jun. 10, 2016.

(51) Int. Cl.
*A61B 8/08* (2006.01)
*G01S 7/52* (2006.01)
*G16H 30/40* (2018.01)

(52) U.S. Cl.
CPC .............. *A61B 8/085* (2013.01); *A61B 8/485* (2013.01); *G01S 7/52022* (2013.01);
(Continued)

(58) Field of Classification Search
CPC ..... A61B 8/085; A61B 8/485; G01S 7/52022; G16H 30/40
See application file for complete search history.

(56) References Cited

U.S. PATENT DOCUMENTS

2007/0276245 A1 11/2007 Konofagou
2009/0112095 A1* 4/2009 Daigle .................... A61B 8/06
600/454

(Continued)

FOREIGN PATENT DOCUMENTS

WO 2014136502 A2 1/2014

OTHER PUBLICATIONS

S. L. Lipman, et al., "Evaluating the Improvement in Shear Wave Speed Image Quality Using Multidimensional Directional Filters [. . . ]," in IEEE Transactions on Ultrasonics, Ferroelectrics, and Frequency Control, Epub Apr. 27, 2016. PMID: 28458448; PMCID: PMC5409160 (Year: 2016).*

(Continued)

*Primary Examiner* — Yi-Shan Yang

(57) ABSTRACT

A system for boundary identification includes a memory (42) to store shear wave displacements through a medium as a displacement field including a spatial component and a temporal component. A directional filter (206, 208) filters the displacement field to provide a directional displacement field. A signal processing device (26) is coupled to the memory to execute a boundary estimator (214) to estimate a tissue boundary in a displayed image based upon a history of the directional displacement field accumulated over time.

13 Claims, 8 Drawing Sheets

(52) U.S. Cl.
CPC ...... *G01S 7/52026* (2013.01); *G01S 7/52042* (2013.01); *G16H 30/40* (2018.01)

(56) References Cited

U.S. PATENT DOCUMENTS

| | | | | |
|---|---|---|---|---|
| 2010/0069751 | A1* | 3/2010 | Hazard | G01S 7/52042 600/438 |
| 2012/0224759 | A1* | 9/2012 | Masui | A61B 8/5269 382/131 |
| 2013/0261452 | A1* | 10/2013 | Tamura | A61B 8/485 600/438 |
| 2015/0005636 | A1* | 1/2015 | Grisan | G06T 7/11 600/443 |
| 2015/0305717 | A1 | 10/2015 | Hollender et al. | |
| 2016/0345939 | A1* | 12/2016 | Toji | A61B 8/5207 |

OTHER PUBLICATIONS

Song, et al., "Comb-Push Ultrasound Shear Elastography (CUSE): A Novel Method for Two-Dimensional Shear Elasticity Imaging of Soft Tissues", IEEE Transactions on Medical Imaging, vol. 31, No. 9, Sep. 2012, pp. 1821-1832.

Song, et al., "Fast Shear Compounding Using Robust 2-D Shear Wave Speed Calculation and Multi-Directional Filtering", Ultrasound in Med. & Biol., vol. 40, No. 6, pp. 1343-1355.

Thomas Deffieux, et al., "On the Effects of Reflected Waves in Transient Shear Wave Elastography", IEEE Transactions On Ultrasonics, Ferroelect, RICS, and Frequency Control, IEEE, 2011.

Song et al: "Comb-Push Ultrasound Shear Elastography (CUSE) With Various Ultrasound Push Beams"; IEEE Transactions On Medical Imaging, vol. 32, No. 8, Aug. 2013, pp. 1435-1447.

* cited by examiner

US 11,337,673 B2

USING REFLECTED SHEAR WAVES FOR MONITORING LESION GROWTH IN THERMAL ABLATIONS

This application is the U.S. National Phase application under 35 U.S.C. § 371 of International Application No. PCT/EP2017/063598, filed on Jun. 5, 2017, which claims the benefit of Provisional Application Ser. No. 62/348,302, filed Jun. 10, 2016. These applications are hereby incorporated by reference herein.

BACKGROUND

Technical Field

This disclosure relates to ultrasound image processing for medical instruments and, more particularly, to detecting boundaries in ultrasound images by directional displacement filtering.

Description of the Related Art

Radiofrequency ablation (RFA) is an effective and widely used treatment modality for liver tumors, where the tumors are heated to the point of coagulation necrosis with an ablation tine inserted to the tumor site. Ultrasound is a frequently used modality for guidance of these procedures; however, currently available ultrasound imaging modalities do not provide sufficient information regarding the thermal lesion created by ablation. Tissue stiffness changes due to the elevated temperatures during RFA. Thermal lesions created by RFA are much stiffer compared to the healthy liver parenchyma and current implementations of shear wave imaging (SWI) elastography and associated reconstruction techniques do not perform well when the stiffness change within the region of interest is substantial. In addition, the presence of an ablation electrode in the field of view (FOV) alters local stiffness conditions and is a major cause for artifacts in SWI for RFA.

SUMMARY

In accordance with the present principles, a system for boundary identification includes a displacement field obtained by storing shear wave displacements through a medium including a spatial component and a temporal component. A directional filter configured to filter the displacement field provides a directional displacement field reflected from a stiff ablation lesion boundary. A boundary estimator is configured to estimate a tissue boundary based upon a history of the directional displacement field accumulated over time.

Another system for boundary identification includes a locally directional displacement field obtained by storing shear wave displacements through a medium including a spatial component and a temporal component. The significant shear wave reflection from a highly stiff ablation boundary is preferentially detected using directional filters configured to filter shear wave displacements to provide a locally directional displacement field. A boundary estimator configured to estimate a stiff tissue boundary based upon a history of the directional displacement field accumulated over time.

Yet another system for boundary identification includes a memory to store shear wave displacements through a medium as a displacement field including a spatial component and a temporal component. A directional filter filters the displacement field to provide a directional displacement field. A signal processing device is coupled to the memory to execute a boundary estimator to estimate a tissue boundary in a displayed image based upon a history of the directional displacement field accumulated over time.

Still another system for boundary identification includes an ultrasound mode to generate shear wave displacements using a push pulse through a medium to generate a displacement field. A signal processing device includes a shear wave imaging module to detect shear wave displacements for a plurality of tracking positions in the medium to generate a displacement field; and a data processing module including at least one directional filter to filter the displacement field to provide a directional displacement field. A boundary estimator estimates a tissue boundary in a displayed image based upon a history of the directional displacement field accumulated over time.

A method for determining a boundary includes generating a shear wave displacement field based on a shear wave through a medium; directionally filtering the shear wave displacement field to create a directionally propagating displacement field; and accumulating an amplitude history of the directionally propagating displacement field to indicate positions of highest amplitude in an image to identify a tissue boundary in the image.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
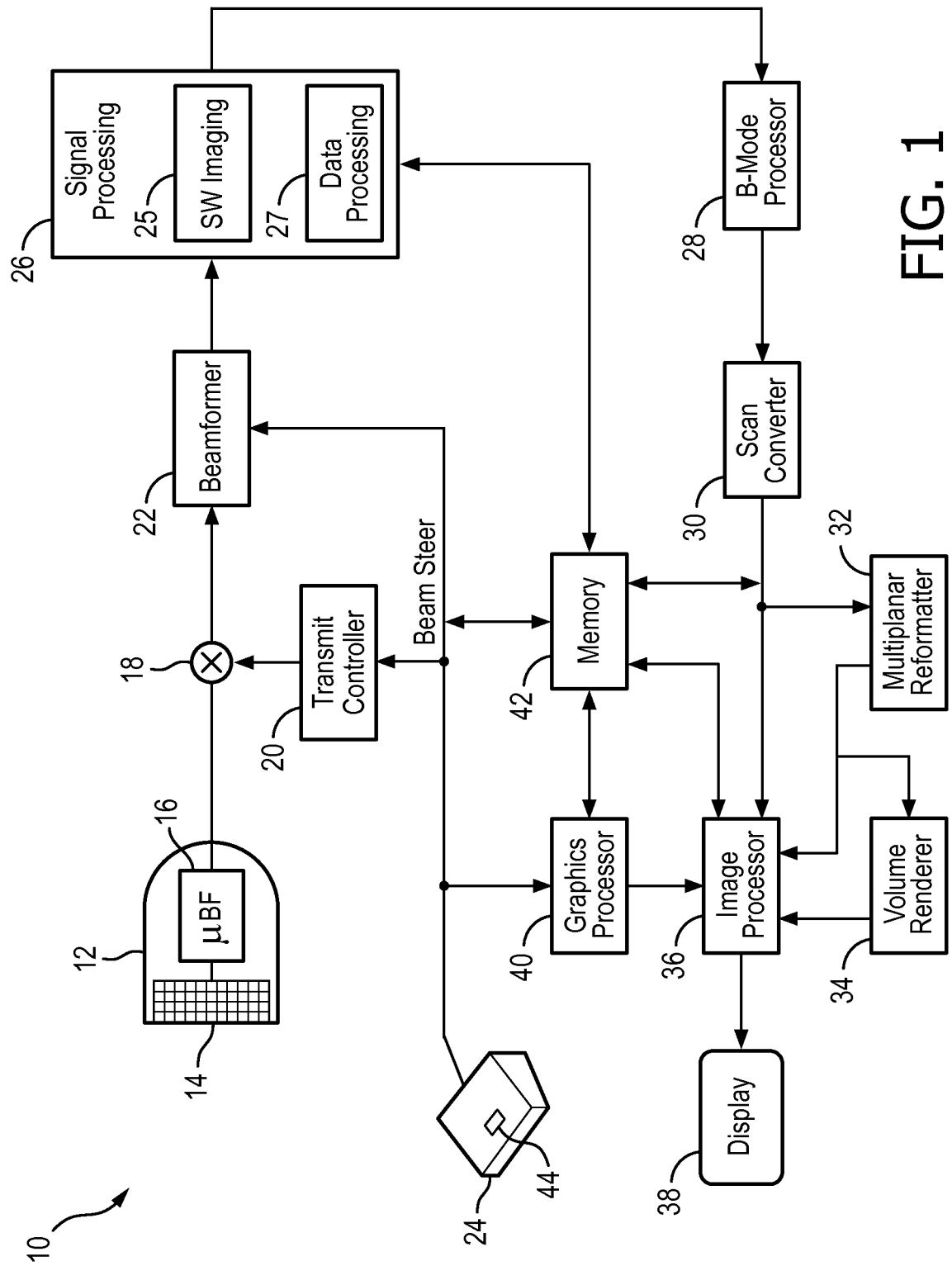
FIG. 1 is a block/flow diagram showing an ultrasound system including boundary identification in accordance with one embodiment.

In accordance with the present principles, a reconstruction for ultrasound shear wave elastography is provided in the presence of very stiff inclusions, such as those generated by radiofrequency ablation (RFA). Due to the elastic mismatch in tissues (e.g., between a thermal lesion and liver parenchyma) a significant fraction of a mechanical wave energy is reflected back from the lesion's boundary. The reflection pattern provides significant information regarding the lesion boundary. In one embodiment, reflected waves are accumulated over time, which forms clutter immediately outside the lesion boundary where the wave has a highest amplitude. In another embodiment, a model, such as a finite element model, may be employed. The model employs the propagating wave field as an input and solves for a reflection boundary, such as the lesion boundary, iteratively to minimize error between estimated reflected waves from the model and measured reflected waves using shear wave imaging. Resulting lesion boundary estimations are processed over time to indicate the expanding ablation area and are displayed for monitoring a treatment progress.

The present approach is particularly effective for detecting very stiff boundaries (such as a thermal ablation zone) due to high detection sensitivity. The high detection sensitivity is due to high-amplitude reflected shear waves that are uniquely present outside the lesion, and reflected shear waves, which have higher displacement amplitudes (in comparison to the lower displacement amplitude inside the stiff ablation zone).

In particularly useful embodiments, RFA treatment protocols employ a simplistic (often ellipsoidal) ablation volume prediction provided in a device manufacturer's specification. Actual treatment volumes may greatly deviate from the prediction, potentially contributing to injury of adjacent anatomy or tumor recurrence after incomplete ablation. Real-time feedback to a clinician may potentially address these clinical challenges. As a widely used guidance tool, ultrasound imaging is an option for real-time ablation monitoring. During RFA procedures, tissue stiffness is elevated due to thermal necrosis. For coagulation zone visualization, the high stiffness contrast between treated and non-treated tissue can be determined using ultrasound elastography.

Real-time monitoring of RFA ensures adequate treatment coverage of tumors. First, a monitoring modality should be highly sensitive for the detection of thermal lesion boundaries, especially, in the presence of a rigid ablation needle. Secondly, the specific approach should be adequate in covering the entire ablation zone. Ultrasound shear wave elastography imaging (SWI) provides robust elasticity estimates in a relatively small region (e.g., compared to a field-of-view of an ultrasound image) by pushing the tissue with acoustic radiation force and imaging the resultant shear wave propagation over time. Tissue elasticity estimates are based on the shear wave propagation speed which is proportional to the tissue elasticity. A time-of-flight (TOF) approach may be used to estimate shear wave speed by measuring the delays between tracking lines perpendicular to the shear wave propagation direction, which is also known as time-to-peak (TTP) reconstruction. Shear wave speed (SWS) estimation can be provided with the TOF approach using the shear wave arrival time determined at multiple spatial locations. By assuming a fixed direction of propagation, the SWS can then be calculated using linear regression.

Tissue elasticity estimates provided by shear wave elastography and TTP rely on the waves travelling in a forward direction, away from a push beam. Inclusions in the SWI region-of-interest that may cause more complicated wave phenomena such as reflection or refraction reduce the performance of these methods. In an attempt to improve the performance of shear wave speed based reconstruction algorithms such as TTP, directional filters may be applied to shear wave displacement maps, which eliminates the reflected waves travelling in the backward direction. However, in the case of stiffer inclusions such as thermal lesions generated by RFA, the shear wave speed estimation of a forward propagating wave approach performs sub-optimally because a significant portion of the wave energy reflects from the inclusion boundary due to elastic mismatch. Additionally, the presence of an ablation needle in the tissue restricts the movement of the surrounding stiff lesion and effectually increases shear stiffness around the lesion, which further diminishes the performance of the traditional shear wave speed based reconstructions. Furthermore, gas bubbles formed during the RFA treatment shadow the field-of-view inside the ablated lesion, which lowers the signal-to-noise-ratio (SNR) of shear wave displacement detection within the lesion and challenges the elastographic reconstruction of the lesion itself. The present principles provide methods for alternative elastographic reconstruction for shear wave imaging of a media with stiffer inclusions, which provide adequate assessment of the expanding thermal ablation boundary.

It should be understood that the present invention will be described in terms of ultrasound imaging instruments; however, the teachings of the present invention are much broader and are applicable to any acoustic imaging instruments. In some embodiments, the present principles are employed in tracking or analyzing complex biological or mechanical systems. In particular, the present principles are applicable to internal tracking procedures of biological systems and procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

It will also be understood that when an element such as a layer, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Referring now to the drawings in which like numerals represent the same or similar elements and initially to FIG. 1, an ultrasound imaging system 10 constructed in accordance with the present principles is shown in block diagram form. The ultrasound system 10 includes a transducer device or probe 12 having a transducer array 14 for transmitting ultrasonic waves and receiving echo information. The transducer array may be configured as, e.g., linear arrays or phased arrays, and can include piezoelectric elements or capacitive micromachined ultrasonic transducers (CMUT) elements. The transducer array 14, for example, can include a two dimensional array (as shown) of transducer elements capable of scanning in both elevation and azimuth dimensions for 2D and/or 3D imaging. The transducer device 12 can be in various forms.

The transducer array 14 is coupled to a microbeamformer 16 in the probe 12, which controls transmission and reception of signals by the transducer elements in the array. In this example, the microbeamformer 16 is integrated with the transducer device 12 and is coupled to a transmit/receive (T/R) switch 18, which switches between transmission and reception and protects a main beamformer 22 from high energy transmit signals. In some embodiments, the T/R switch 18 and other elements in the system 10 can be included in the transducer probe 12 rather than in a separate ultrasound system base. The transmission of ultrasonic beams from the transducer array 14 under control of the microbeamformer 16 is directed by a transmit controller 20 coupled to the T/R switch 18 and the beamformer 22, which may receive input from the user's operation of a user interface or control panel 24.

One function controlled by the transmit controller 20 is the direction in which beams are steered. Beams may be steered straight ahead from (orthogonal to) the transducer array 14, or at different angles for a wider field of view. The partially beamformed signals produced by the microbeamformer 16 are coupled to a main beamformer 22 where partially beamformed signals from individual patches of transducer elements are combined into a fully beamformed signal. The transducer device or probe 12 is capable of creating shear waves with a relatively larger coverage area (e.g., 2-3 cm's wide). The transducer device 12 can create a push pulse, which is positioned outside an anticipated lesion area. The push pulse creates local tissue displacement at or around the transmit focus resulting in shear displacements and shear wave propagation that can be obtained by tracking pulses, radiofrequency (RF) data acquisition and signal processing.

The beamformed signals are coupled to a signal processing device 26. The signal processing device or processor 26 can process the received echo signals in various ways, such as bandpass filtering, decimation, I and Q component separation, and harmonic signal separation. The signal processor 26 may also perform additional signal enhancement such as speckle reduction, signal compounding, and noise elimination.

In accordance with the present principles, the signal processor 26 includes a shear wave imaging module 25 configured to create shear wave displacements and image the shear waves at high resolution with the larger coverage area (e.g., 2-3 cm's wide). A data processing module 27 is included in the signal processor 26 for applying directional filters to the resulting displacement field to separate the field into forward propagating and backward propagating waves. A processing algorithm (e.g., accumulation method) for estimating the stiff lesion boundary based on how the reflected field is generated from the forward propagating field is also included. For example, peaks, magnitudes or other characteristics of propagating wave displacements can be stored to create displacement fields or maps. The accumulated (stored) data can be mapped for corresponding positions in the propagation medium.

The processed signals are coupled to a B mode (or other mode) processor 28, which can employ amplitude detection for the imaging of structures in the body. The signals produced by the B mode processor are coupled to a scan converter 30 and a multiplanar reformatter 32. The scan converter 30 arranges the echo signals in the spatial relationship from which they were received in a desired image format. For instance, the scan converter 30 may arrange the echo signal into a two dimensional (2D) sector-shaped format, or a pyramidal three dimensional (3D) image. The multiplanar reformatter 32 can convert echoes, which are received from points in a common plane in a volumetric region of the body into an ultrasonic image of that plane.

A volume renderer 34 converts the echo signals of a 3D data set into a projected 3D image as viewed from a given reference point. The 2D or 3D images are coupled from the scan converter 30, multiplanar reformatter 32, and volume renderer 34 to an image processor 36 for further enhancement, buffering and temporary storage for display on an image display 38. A graphics processor 40 can generate graphic overlays for display with the ultrasound images. These graphic overlays or parameter blocks can include, e.g., standard identifying information such as patient name, date and time of the image, imaging parameters, frame indices and the like. For these purposes, the graphics processor 40 receives input from the user interface 24, such as a typed patient name. The user interface 24 can also be coupled to the multiplanar reformatter 32 for selection and control of a display of multiple multiplanar reformatted (MPR) images.

In accordance with the present principles, ultrasound data is acquired and stored in memory 42. The memory 42 is depicted as being centrally placed; however, the memory 42 may store data and interact at any position in the signal path. The memory 42 is configured to store programs and applications (e.g., accumulation of displacement data in maps or look up tables). A graphics processor 40 and/or the image processor 36 make image adjustments in accordance with image signals. The display 38 provides for ablation monitoring, which is updated at every acquisition frame with expanding lesion boundary. The display 38 may also permit a user to interact with the system 10 and its components and functions, or any other element within the system 10. This is further facilitated by the interface 24, which may include a keyboard, mouse, a joystick, a haptic device, or any other peripheral or control to permit user feedback from and interaction with the system 10.

In accordance with the present principles, shear wave generation and detection is provided using system 10. A high amplitude and long duration (e.g., 1 ms) push pulse is transmitted by the probe 12 to create enough acoustic radiation force in tissue (being imaged) to displace the tissue adequately (e.g., on the order of microns). Once the force is removed, the displacement propagates in the form of a shear wave, perpendicular to the push direction. The shear wave propagation has a reasonably high signal-to-noise ratio (SNR) to be detected by tracking pulses with high pulse repetition frequency (e.g., 1.5 kHz), for about 2-3 cm's away from the pushing line. 'n' number of tracking pulses may be employed to cover a lateral extent of a region of interest (ROI) and the tracking is repeated for 'm' time points to acquire an entire displacement history for each tracking position, which can be stored in memory 42. In one useful embodiment, the push pulse is placed outside an anticipated lesion boundary, such that the boundary is placed about halfway through the detection range.

During imaging operations, a user may need to determine a boundary in an image or images. In accordance with one embodiment, a boundary detection mode may be activated by using a manual or software switch 44 to enter this mode. In the boundary detection mode, a greater sensitivity is provided for detecting a boundary by employing shear wave displacements and directional displacement filters in the signal processing device 26 as described. The signal processing device 26 provides a boundary estimator to decipher or delineate a boundary between tissues.

The signal processing device 26 may include a computer readable storage medium (or media) having computer readable program instructions thereon for causing a processor to carry out aspects of the present principles. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. The computer readable storage medium may include: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic or acoustic waves.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network interface in each computing/processing device receives computer readable program instructions from the network and forwards the computer readable program instructions for storage in a computer readable storage medium within the respective computing/processing device. In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present principles.

Figure 2:
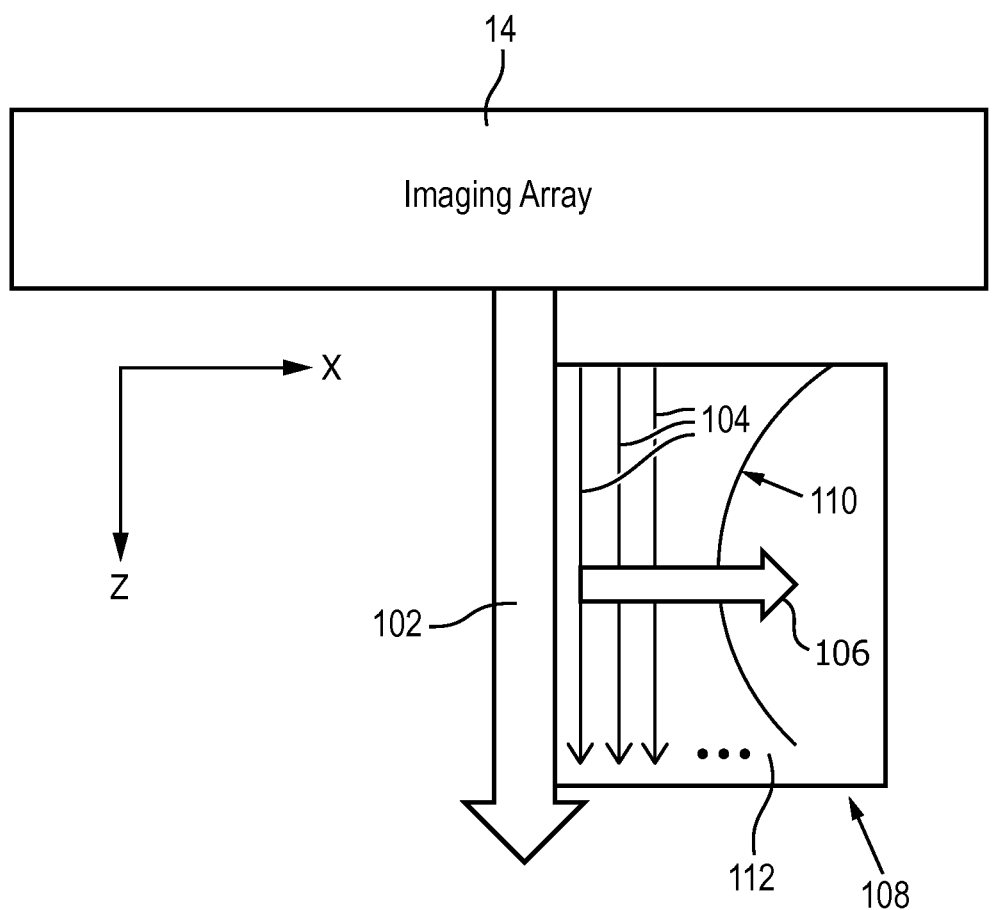
FIG. 2 is a diagram showing shear wave interactions in a medium in accordance with one embodiment.

Referring to FIG. 2, a schematic layout of a push pulse 102 with tracking pulses 104 is illustratively depicted in accordance with the present principles. Imaging array 14 (FIG. 1) is held in contact with tissue 112 at or near a lesion boundary 110. In one useful embodiment, the push pulse 102 is placed outside the lesion boundary 110 so that the boundary 110 is about halfway through a tracking range 108 of a shear wave 106. The push pulse 102 is transmitted at a high amplitude and long duration (e.g., ~1 ms) to create enough acoustic radiation force in tissue 112 to displace the tissue 112, e.g., at least one micron. Displacement is propagated in the form of the shear wave 106, which moves perpendicular to a push direction of the push pulse 102. The shear wave 106 propagation has a SNR that can be detected by tracking pulses or lines 104 with a high pulse repetition frequency (e.g., 1.5 kHz), for about 2-3 cm's away from the pushing line.

Acoustic output settings of the ultrasound scanner, such as the push pulse amplitude or tracking pulse amplitude, as well as the pulse sequence may be default values to the shear wave imaging modality and not specific to the reflected wave method. These settings are preferably within approved limits of the US Food and Drug Administration (FDA) (i.e., Mechanical Index≤1.9).

A number of tracking pulses 'n' may be employed sufficient to cover a lateral extent of a region of interest (ROI) (tracking range 108), and the tracking is repeated for 'in' time points to acquire an entire displacement history for each tracking position (corresponding to each tracking line 104). The displacement history for a 2D or 3D region may be performed.

Shear wave displacements can be detected using speckle tracking algorithms executed by the signal processor 26 (FIG. 1) from the tracking data. Data processing 27 (FIG. 1) may include at least one directional filter (preferably two, although more may be employed) that are applied to the resulting displacements. Any combination of spatial and temporal filters in the frequency domain can be applied; however, the illustrative embodiment described employs a spatio-temporal filter in the lateral x-direction (parallel to the shear wave propagation direction) and time. Filters are applied to the shear displacements at each depth point (for a total of 'd' number of points in the z-direction) to obtain forward and backward propagating waves along the x-axis.

Figure 3:
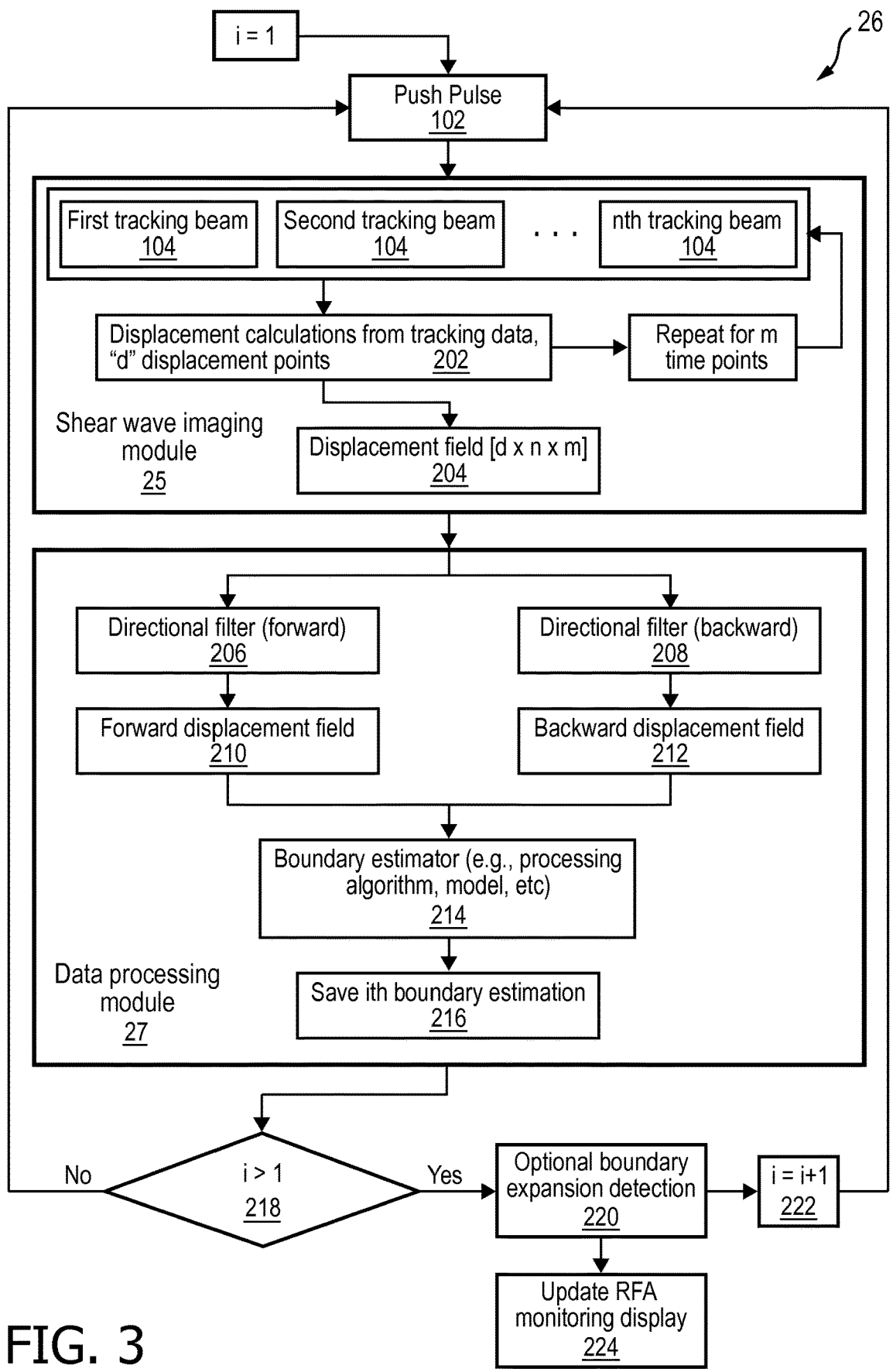
FIG. 3 is a block/flow diagram showing a system/method for boundary identification in greater detail in accordance with one embodiment.

Referring to FIG. 3, a block/flow diagram showing data acquisition and processing performed by the signal processing device 26 using forward and backward propagating waves for RFA lesion estimation is illustratively depicted. The signal processing device 26 may include hardware and/or software. In one particularly useful embodiment, the signal processing device 26 includes one or more processors and memory. The memory may include integrated memory, an external memory (42, FIG. 1) or combinations thereof.

A push beam 102 is initiated (counter i=1) by an ultrasound probe 12 (FIG. 1) and provides n tracking beams 104. The push beam 102 may include, e.g., an amplitude of between about 0.5 to about 10 microns for duration of about 1 ms. Other pulse amplitudes and durations may also be employed.

The push pulse 102 is monitored along a plurality (n) of tracking lines 104 to capture the spatial aspect of the shear wave displacements. Results for each tracking line position are repeated m times to capture the temporal aspects of the shear wave displacements. Tissue displacement calculations are performed in block 202 from the tracking data for "d" depth (along the push pulse travel direction) displacements points. This identifies or defines a displacement field over time, e.g., defined by d×n×m in block 204. The displacement field over time is stored to provide an accumulated history. The displacement field over time may be stored in a buffer or other memory elements (e.g., memory 42 in FIG. 1).

In ultrasound shear wave elastography (SWE), the complex wave field due to reflections and refractions are indicated to be a source of low SNR and artifacts, therefore directional filters are employed to separate and eliminate these reflections and improve reconstruction algorithm performances.

A 2-dimensional spatio-temporal directional filter (see e.g., FIG. 4) is applied to the data for filtering forward or backward propagating waves. For the described embodiment, since the primary spatial propagation direction of shear wave motion is in the lateral direction (x-dimension) over time (t-dimension), the directional filters are applied to the 2D space including both x and t dimensions. Furthermore, filtering is performed to x-t data at each point in the depth direction (y-dimension). Any combination of time and space directions is possible for directional filtering. Directional filters 206, 208 may be digitally implemented and may be applied to images or other data. In one embodiment, the directional filters 206 search for edges within an image when a large change (a steep gradient) occurs between adjacent pixel values. This change in values is measured by the first derivatives (or slopes) in image data.

Due to the highly dispersive and attenuating nature of shear waves, the highest displacements and most definite wave fronts are observed closer to the source. Similarly for reflected shear waves, the highest displacement amplitude is observed closer to the reflecting boundary After the shear wave data is acquired and processed as described, a directional filter forward 206 is applied to the data to determine a forward displacement field 210. The forward displacement field 210 may include a 2D Fourier transform or other transform or data processing applied to the data to differentiate/filter forward propagating waves (through space and time progression). For each depth point (d), a 2D FFT is applied to the data in x-t space to obtain the ωk-frequency domain data. A precomputed frequency domain filter specific to a directionality of wave propagation is multiplied with the FFT of the data. The precomputed directional filters may take the form of a checkerboard pattern as illustrated in FIG. 4, or may take other forms.

Figure 4:
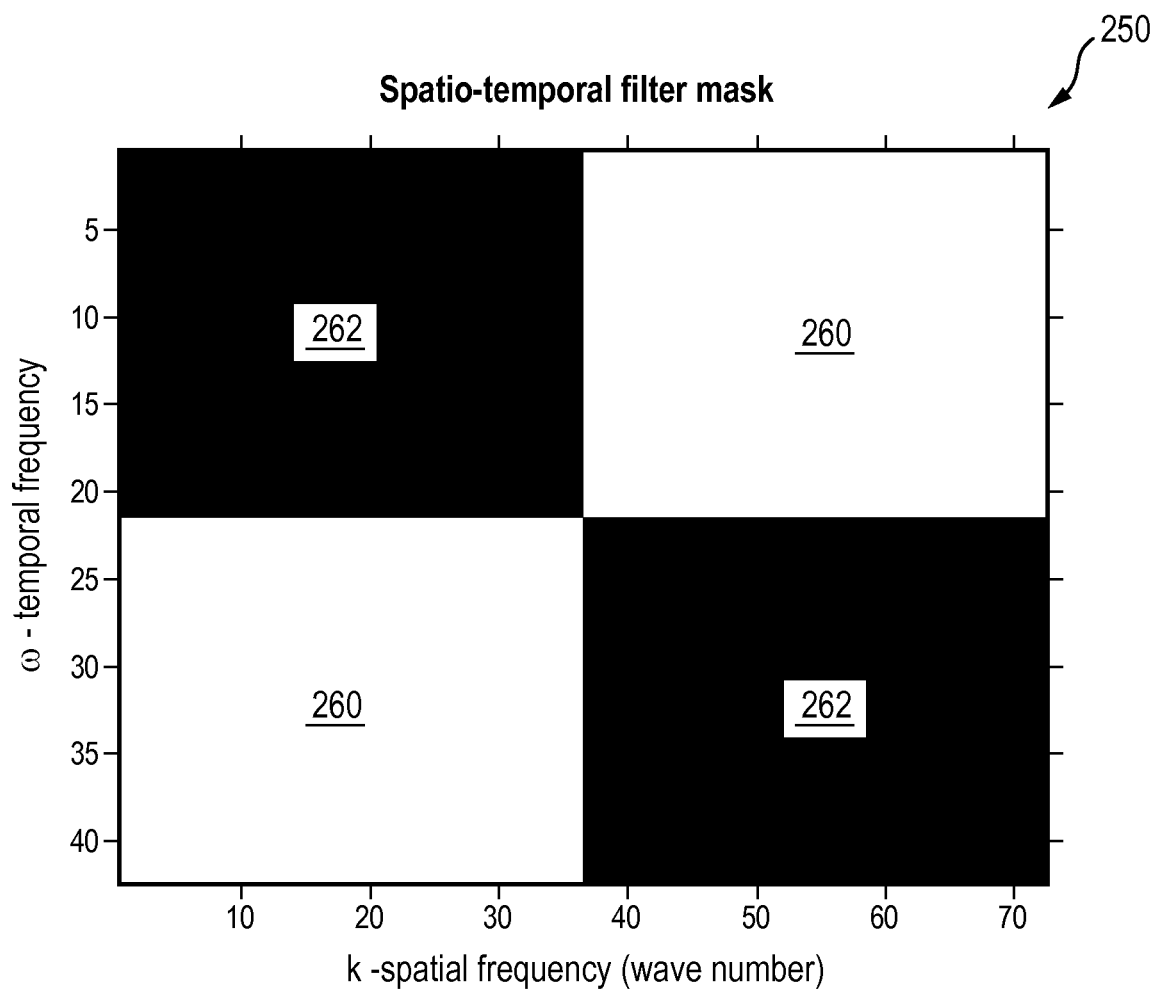
FIG. 4 is a diagram showing an illustrative filter employed for directional filtering of displacement data in accordance with one embodiment.

In FIG. 4, a spatio-temporal filter mask 250 is illustratively shown with temporal frequency (ω) on the y-axis versus spatial frequency (wavenumber (k)) on the x-axis. White regions 260 indicate a value of 1 representing a part of the ωk-frequency domain to be kept, and black regions 262 indicate zero values of the filter where the signals are filtered-out for forward propagating waves. The transitions between the black and white regions are smoothed properly to avoid filtering artifacts, such as the Gibbs phenomenon. The mirror image of this filter where white regions 260 are black, and black regions 262 are white from the image of FIG. 4 is employed for backward propagating waves. An Inverse FFT may be performed to obtain filtered x-t space data. This data includes waves propagating in a single direction (forward in this case).

Likewise, in FIG. 3, a directional filter backward 208 is applied to the data to determine a backward displacement field 212. In the case of stiffer inclusions such as thermal lesions generated by RFA, the shear wave speed estimation of a forward propagating wave approach may not be enough since a significant portion of the wave energy reflects from the inclusion boundary due to elastic mismatch. It should be understood that the forward and backward directions are employed for convenience and any two propagating directions may be employed. It is also preferable that the directions be spatially opposite to one another. The backward displacement field 212 may include a 2D Fourier transform or other transform or data processing applied to the data to differentiate/filter backward propagating waves (through space and time progression). For each depth point (d), a 2D FFT is applied to the data in x-t space to obtain the ωk-frequency domain data. A precomputed frequency domain filter specific to a directionality of wave propagation is multiplied with the FFT of the data. The precomputed directional filters may take the form of a checkerboard pattern opposite that as illustrated in FIG. 4, e.g., black regions 262 indicate a value of 1 representing a part of the ωk-frequency domain to be kept, and white regions 260 indicate zero values of the filter where the signals are filtered-out for backward propagating waves. The transitions between the black and white regions are smoothed properly to avoid filtering artifacts, such as the Gibbs phenomenon. An Inverse FFT may be performed to obtain filtered x-t space data. This data includes waves propagating in a single direction (backward in this case).

The signal processing device 26 coupled to the memory to execute a boundary estimator 214 to estimate a tissue boundary in a displayed image based upon a history of the directional displacement field accumulated over time. The boundary estimator 214 accumulates an amplitude history of the directionally propagating displacement field to indicate positions of highest amplitude in an image to identify a tissue boundary in the image. The boundary estimator 214 may include different forms, such as, an image processing program, a data processing program, a model, such as, e.g., a finite element model, a solver, etc. In useful embodiments, the boundary estimator 214 includes a processing algorithm or model to estimate the tissue boundary based upon the forward displacement field 210 and/or the backward displacement field 212. The boundary estimator 214 includes an accumulation method that counts or accumulates measured intensity, energy etc. over time. With the passing of waves, both forward and backward amplitude traces can be recorded (buffered) to evaluate the regions where the most energy has passed. Since the lesion boundary has a higher stiffness, the forward and backward displacement field should provide redundant information about the lesion boundary where a clutter of reflected waves is obtained in front of the lesion boundary, where they have the highest amplitude (highest intensity accumulated over time). In one embodiment, the boundary estimator 214 relies on the accumulation of backward propagating wave amplitudes due to a reflection from a boundary. In one embodiment, the history of wave amplitudes is summed after directional filtering. This gives significant contrast right outside the inclusion where the reflected waves have the highest amplitude, forming a clutter indicating a reflecting boundary.

A boundary estimation (BE) is saved in memory in block 216 and processing continues to decision block 218. In decision block 218, a determination is made as to whether i (the counter) is greater than 1. If i is not greater than 1, then the path returns to generate a push beam. If i is greater than 1, the path goes to block 220. Other iteration schemes may also be employed.

In block 220, processing provides the lesion boundary as well as other inclusions for potential reflectors due to tissue inhomogeneity. In the case of RFA, an actual lesion boundary expands with time, therefore the acquisitions and processing is repeated after a brief amount of time (e.g., 2-3 sec), while keeping the ultrasound probe stationary. Repeat measurements will give the same solution for intrinsic reflectors; however, the thermal lesion boundary will expand over several repeat measurements, therefore an optional addition to the processing may be to detect the shift of the lesion boundary over several repeat cycles, using subtraction ($BE_i-BE_{i-1}$) or cross-correlation (lag($BE_i$, $BE_{i-1}$)). This additional processing will cancel the intrinsic reflectors from the tissue and provide the growing lesion boundary. A small amount of motion induced shift between measurements can be compensated by image registration. At this point the lesion boundary is sent to the RFA monitoring display unit to provide feedback for the treatment in block 224. In block 222, the iteration counter is incremented and the path returned to generate a new push beam 102.

In one embodiment for boundary estimation, a model based wave equation can be solved in boundary estimator 214 with the forward and backward propagating waves as input and outputs to the model, respectively. The model may include a finite element model that can be employed to simulate transient dynamics of the shear wave propagation. Healthy tissue stiffness is estimated from the forward propagating waves using a reconstruction algorithm, in block 214, such as time-to-peak (TTP) reconstruction, and lesion stiffness is assumed to be much greater than the healthy tissue stiffness (e.g., 3 times the healthy tissue stiffness). Using these material properties, the model's geometric parameters (location for lesion boundary) are optimized to minimize the error between the simulated reflected waves (from the model solution) and the measured reflected waves (from shear wave imaging). An optimal solution for the lesion boundary is stored in the memory buffer and processed similarly for display. The present principles may be carried out in a plurality of ways and may include different output configurations and goals.

Figure 5:
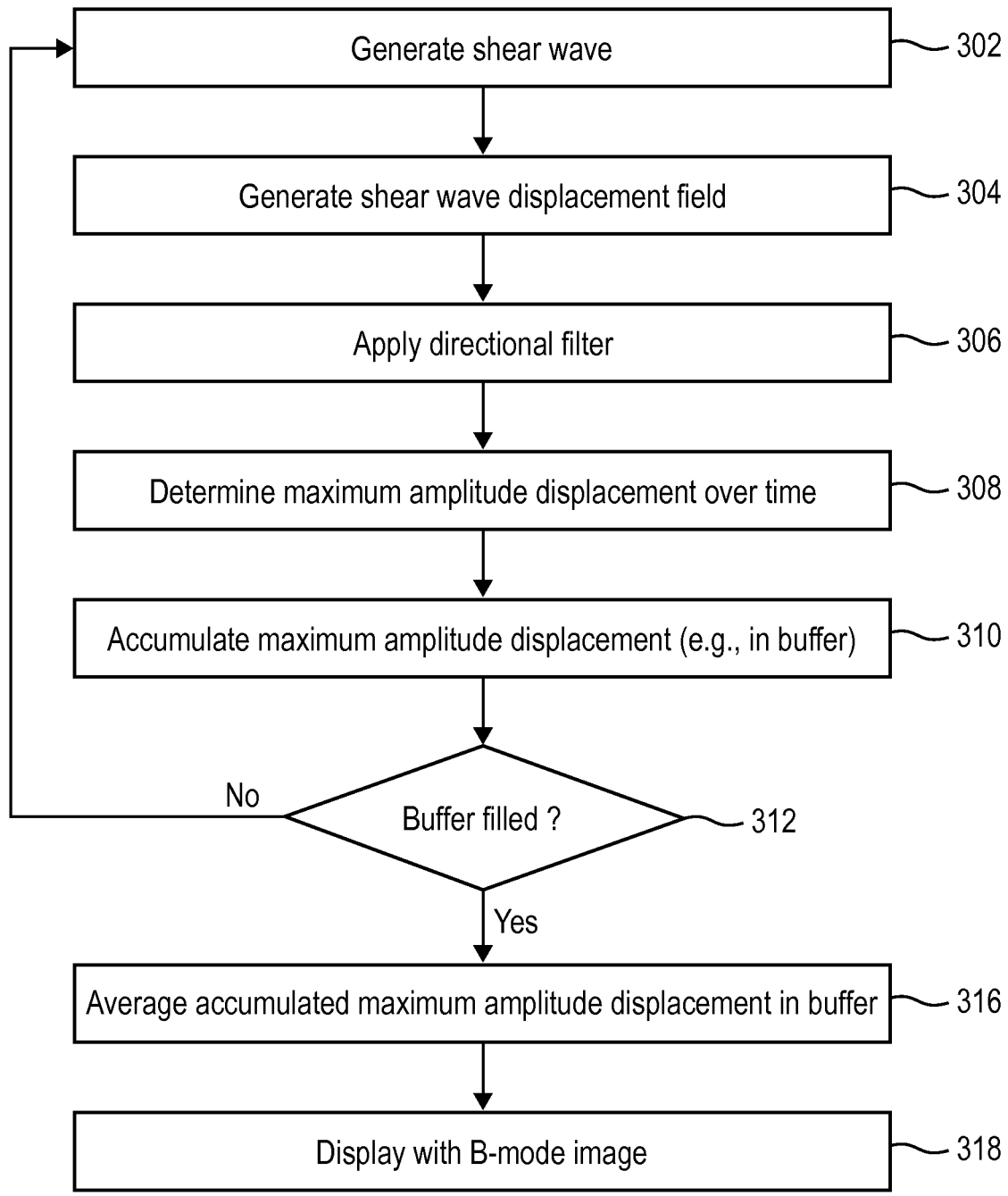
FIG. 5 is a block/flow diagram showing a method for boundary identification for creating a composite image in accordance with one embodiment.

Referring to FIG. 5, in one embodiment, the lesion boundary may be displayed as an overlay jointly with or superimposed on a conventionally acquired B-mode image. In block 302, a push beam is sent to generate a shear wave. In block 304, a 3D (2 space dimensions and time) shear wave displacement field D (d=1 ... numDepths, n=1 ... numX, m=1 ... numTime) is obtained, where numDepth is the number of depths points, numX is the number of lateral sampling points, and numTime is the number of time points at which to sample the shear wave displacements. In block 306, a directional filter (backward or forward or both) is applied for each plane at depth d, D(d, x=1 ... numX, t=t.numTime). This creates the backward-propagating displacement field $D_{back}$ (d=1 ... numDepths, n=1 ... numX, m=1 ... numTime). In block 308, a maximum displacement amplitude across all time points is computed, e.g., $D_{back,max}$ (d=1 ... numDepths, n=1 ... numX). In block 310, $D_{back,max}$ is accumulated in a circular ring buffer with N elements, overwriting the oldest element if the ring buffer is already filled. Illustrative values for N are [2 ... 10]. In block 312, if there are fewer than N elements in the buffer, go to block 302 to generate a new displacement field. If the buffer is filled (has N elements), continue with block 316.

In block 316, average the buffered $D_{back,max}(1 ... N)$ to find $D_{back,max,avg}$(d=1 ... numDepths, n=1 ... numX). In block 318, display $D_{back,max,avg}$ (jointly with/superimposed on an acquired B-mode image).

Figure 6:
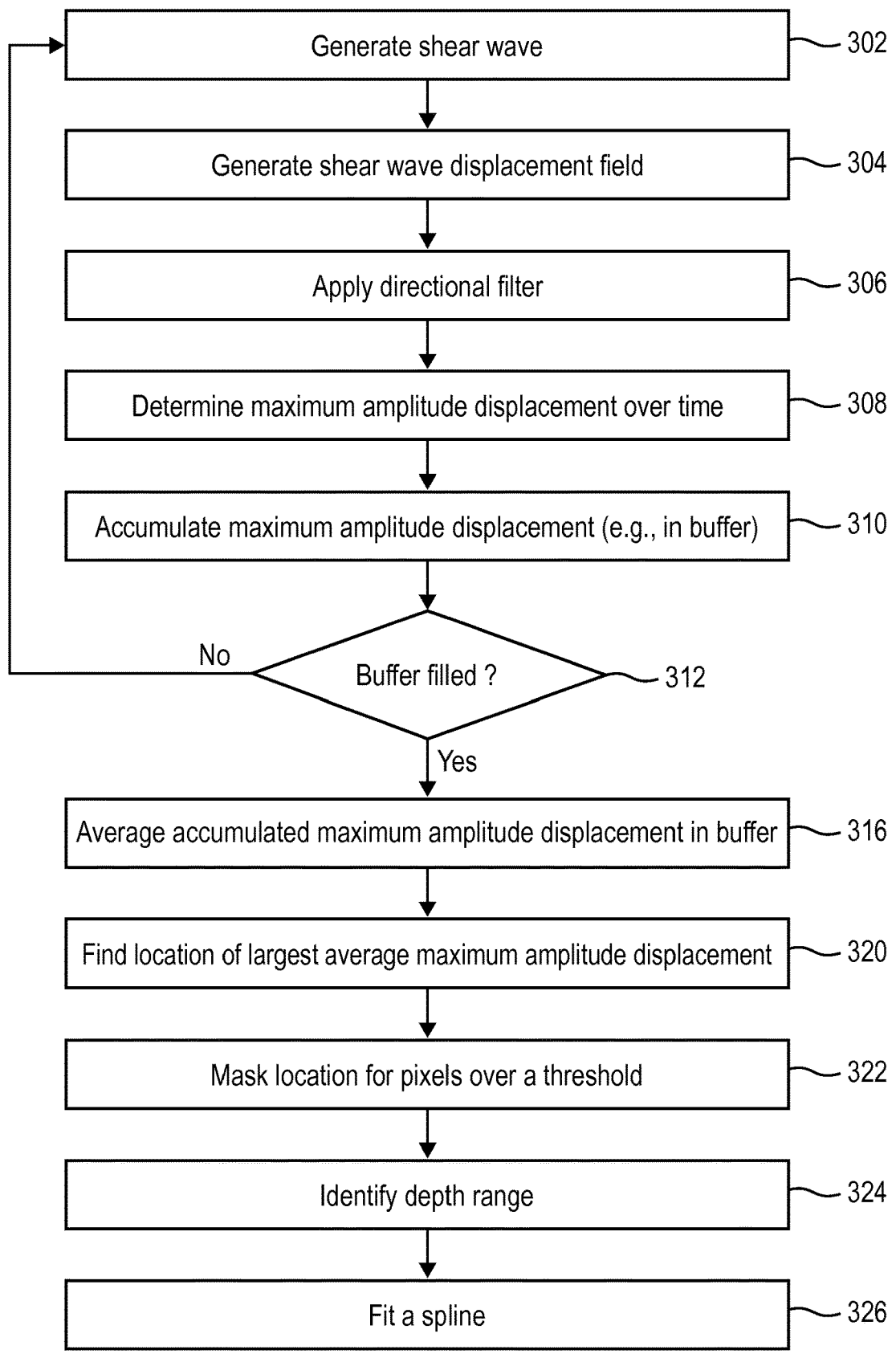
FIG. 6 is a block/flow diagram showing a method for boundary identification for generating a spline to define the boundary in an image in accordance with one embodiment.

Referring to FIG. 6, in another embodiment, a lesion boundary is estimated and displayed instead of displaying averaged maximum backward-propagating amplitudes. Here, blocks 302 through 316 of FIG. 5 remain the same, and the path proceeds with block 320. In block 320, a location $d_{max}$, $x_{max}$ of largest $D_{back,max,avg}$ is found in the data. In block 322, the area of the location in $D_{back,max,avg}$, is masked keeping only those pixels for which the amplitude is larger than a threshold (e.g., ½ the maximum amplitude). In block 324, identify the depth range $d_1 ... d_2$ around $d_{max}$ for which all pixels are, e.g., >½ the maximum amplitude. In block 326, for each depth $d_i$ in $d_1 ... d_2$, identify the x value $x_i$>½ $x_{max}$ at which the amplitude falls off to <½ the maximum amplitude. In block 326, fit a spline through the points ($d_i$, $x_i$), and display this spline as the estimate of the lesion boundary.

Figure 7:
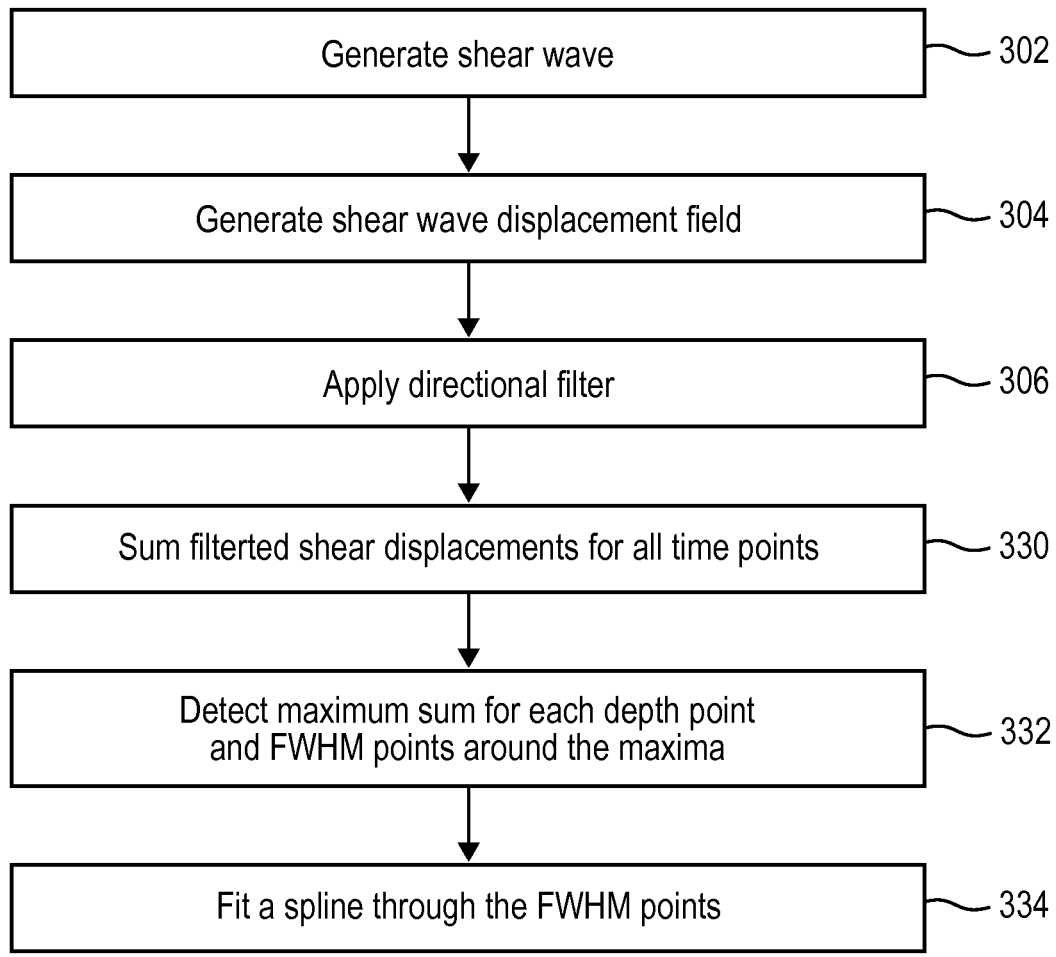
FIG. 7 is a block/flow diagram showing another method for boundary identification for generating a spline to define the boundary in an image in accordance with one embodiment.

Referring to FIG. 7, in another embodiment, the lesion boundary is estimated and displayed instead of displaying averaged maximum backward-propagating amplitudes using a different methodology. Here, blocks 302 through 306 of FIG. 5 remain the same, and the path proceeds with block 330. In block 330, sum backward (or forward) filtered shear displacements for all numTime points, i.e., $\Sigma_t\, D_{back}$ (d=1 . . . numDepths, n=1 . . . numX, t) to obtain a single shear displacement field image $D_{sum}$. In block 332, detect the maximum of $D_{sum}$ for each depth point, $(d_i, x_{max@di})$ also detect the full width half maximum (FWHM) points around the maxima $(d_i, x_{FWHM\_1@di}\; \&\; d_i, x_{FWHM\_2@di})$. In block 334, fit a spline through the FWHM points on the opposite side of the push pulse $(d_i, x_{FWHM\_2@di})$ and estimate the lesion boundary.

These methods are illustrative of ways of defining and displaying lesions boundaries. The methods should not be construed as limiting and other methods of data processing and imaging may be employed in accordance with the present principles.

Figure 8:
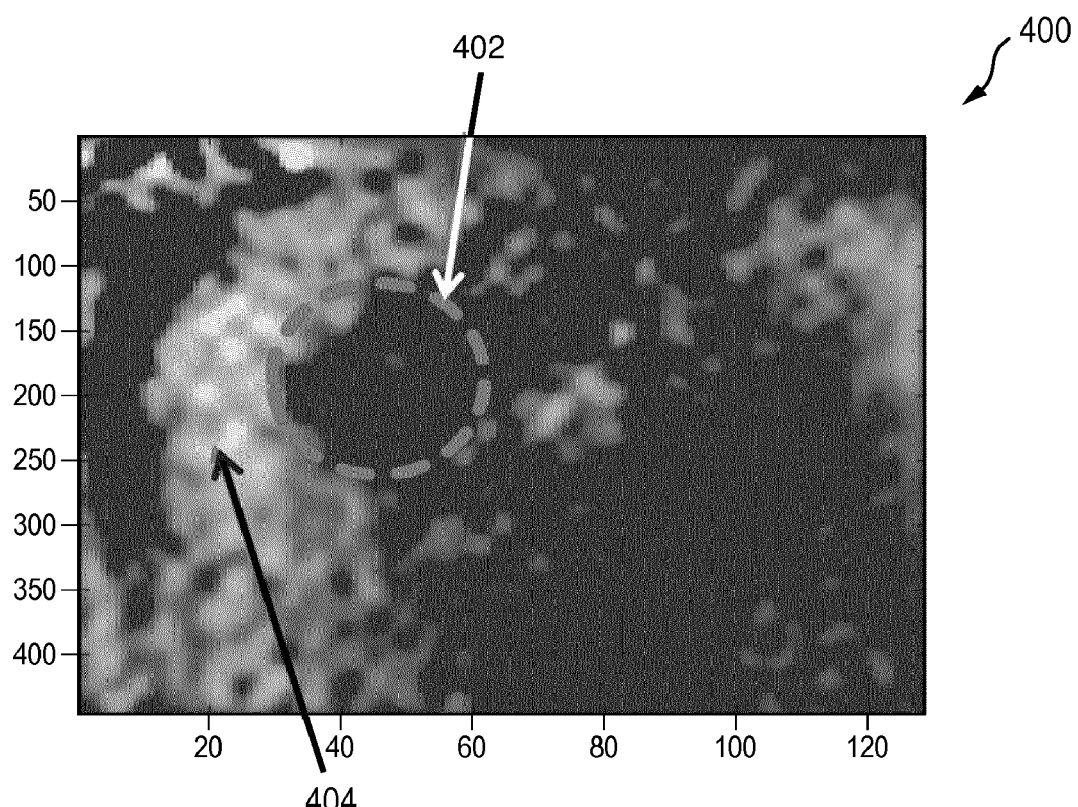
FIG. 8 is an image showing displacement amplitude data to delineate a lesion boundary in accordance with the present principles.

Referring to FIG. 8, results 400 of post processing of the reflected/backward propagating waves for boundary detection are shown in accordance with one illustrative embodiment. Despite the less stiff nature of this inclusion, compared to a typical thermal lesion generated by RFA, a clutter of reflected waves 404 is obtained in front of a lesion boundary, where they have a highest amplitude. A lesion 402 is indicated with a dashed circle, and reflected wave clutter 404 delineates its boundary. Elastic modulus results are in Pascals (Pa).

Figure 9:
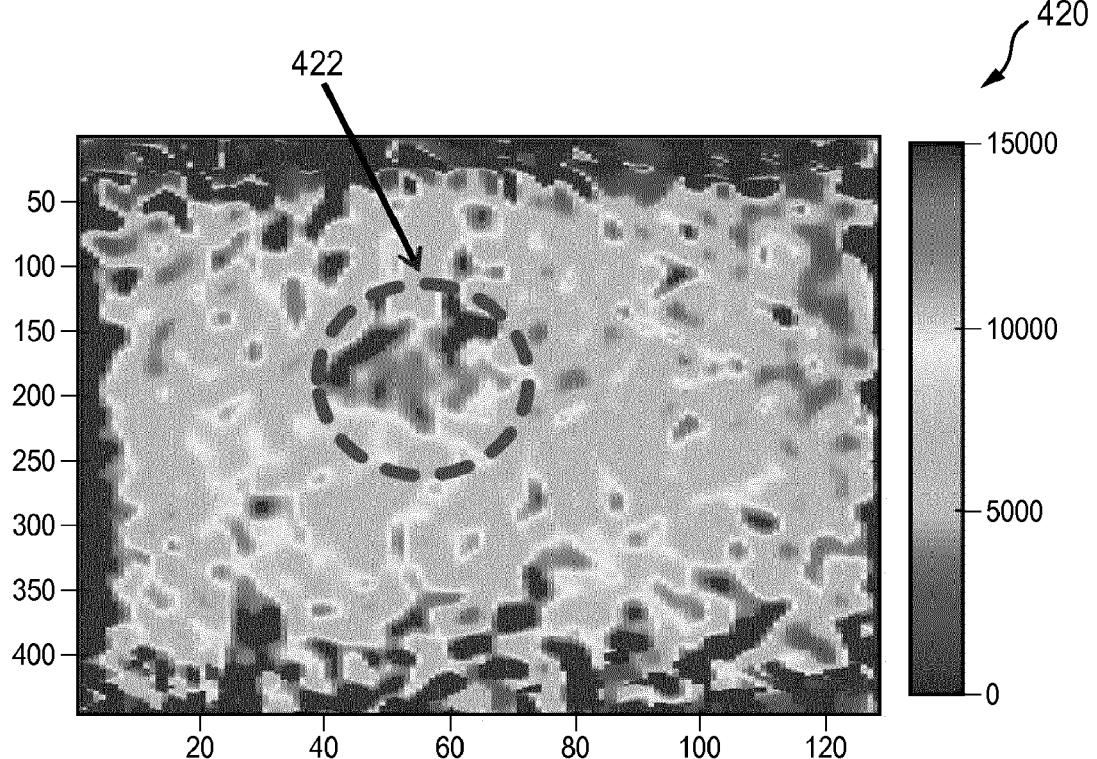
FIG. 9 is an image showing a delay-based elastography reconstruction of the data of FIG. 8 to delineate the lesion boundary in accordance with the present principles.

Referring to FIG. 9, a time-delay based elastography reconstruction 420 is shown for a same dataset as results 400 in FIG. 8, indicating the lesion 422. Elastic modulus results are in Pa. The reconstruction 420 shows the time-delay based reconstruction using the forward propagating waves only. Regular elastography reconstruction still performs well with this dataset because the stiffness difference between the lesion and the background is within reasonable limits (e.g., 15 kPa versus 7.5 kPa). The boundary estimated through reflected wave approach (FIG. 8) conforms to the shape of the lesion visible in the elastography reconstruction (FIG. 9). The wide clutter 404 can be segmented and its far end, further away from the push pulse location is marked as the lesion boundary, as provided with reference to FIG. 7.

The present principles can provide and display elasticity maps for lesion growth estimation and ablation monitoring procedures. In particular, the present principles result in an image that highlights (stiff) boundaries, where shear wave reflections occur, rather than providing stiffness estimates throughout the field of view. This may be examined in tests using phantoms with very stiff inclusions, e.g., if the boundary visualization improves with increasing stiffness of the inclusion, the reflected wave processing is advantageously employed. Methods of ablation therapy monitoring can be applied to any device used for RF ablation monitoring. Moreover, a same approach may also be employed with other forms of heat based thermal ablative therapy such as microwave, high-intensity focused ultrasound (HIFU), etc. In addition to thermal therapy monitoring, the present embodiments can be applied to image guided biopsy applications where an effective stiffness of the biopsy target is increased due to the presence of a needle or other device.

In interpreting the appended claims, it should be understood that:
  a) the word "comprising" does not exclude the presence of other elements or acts than those listed in a given claim;
  b) the word "a" or "an" preceding an element does not exclude the presence of a plurality of such elements;
  c) any reference signs in the claims do not limit their scope;
  d) several "means" may be represented by the same item or hardware or software implemented structure or function; and
  e) no specific sequence of acts is intended to be required unless specifically indicated.

Having described preferred embodiments for reflected shear waves for monitoring lesion growth in thermal ablations (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for boundary identification, comprising:
a memory configured to store shear wave displacements through a medium as a displacement field including a spatial component and a temporal component;
two directional filters configured to filter the displacement field to provide directional displacement fields; and
a signal processing device coupled to the memory, the memory having instructions stored therein that when executed by the signal processing device cause the signal processing device to estimate a tissue boundary in a displayed image by summing amplitude readings of repeated measurements of propagating waves generated by corresponding push pulses and detected within the directional displacement fields over time and define a spline through amplitude data of the amplitude readings to indicate the tissue boundary, wherein the spline is provided on the displayed image.

2. The system as recited in claim 1, further comprising an ultrasound probe configured to generate the push pulses configured to generate the shear wave displacements for the displacement field.

3. The system as recited in claim 1, wherein the two directional filters include a forward propagating filter configured to filter the displacement field to provide a forward propagating displacement field as one of the directional displacement fields.

4. The system as recited in claim 1, wherein the two directional filters include a backward propagating filter configured to filter the displacement field to provide a backward propagating displacement field as one of the directional displacement fields.

5. The system as recited in claim 1, wherein the two directional filters include a forward and a backward propagating filter configured to filter the displacement field to provide a forward and backward propagating displacement field as the directional displacement fields.

6. The system as recited in claim 1, wherein the boundary estimator includes a model to estimate the tissue boundary using a propagating wave field as an input and iteratively solving for reflected waves to minimize error between estimated reflected waves from the model and measured reflected waves using shear wave imaging.

7. The system as recited in claim 1, wherein the instructions further cause the signal processing device to estimate the tissue boundary based upon pixel clutter indicating a history of shear wave amplitudes.

8. The system as recited in claim 1, wherein the system includes an ultrasound imaging system having a boundary estimator mode that estimates the tissue boundary in the displayed image when the boundary estimator mode is activated.

9. The system as recited in claim 1, further comprising:
an ultrasound mode to generate the shear wave displacements using the push pulses through the medium to generate the displacement field, wherein the signal processing device comprises:
  a shear wave imaging module configured to detect shear wave displacements for a plurality of tracking positions in the medium to generate the displacement field; and
  a data processing module including the two directional filters configured to filter the displacement field to provide the directional displacement fields, the data processing module including the boundary estimator.

10. The system as recited in claim 9, wherein the instructions further cause the signal processing device to estimate the tissue boundary based upon pixel clutter indicating a history of shear wave amplitudes.

11. The system as recited in claim 9, wherein the ultrasound mode includes a boundary estimator mode that estimates the tissue boundary in the displayed image when the boundary estimator mode is activated.

12. A method for determining a boundary, comprising:
generating a shear wave displacement field based on a shear wave through a medium;
directionally filtering the shear wave displacement field using a first directional filter and a second directional filter to create directionally propagating displacement fields, wherein the first and second directional filters filter in spatially different directions;
summing amplitude readings of repeated measurements of propagating waves generated by corresponding push pulses and detected within the directionally propagating displacement fields to indicate positions of highest amplitude in an image to identify a tissue boundary in the image;
defining a spline through amplitude data of the amplitude readings to indicate the tissue boundary; and
displaying the spline on the image.

13. The method as recited in claim 12, wherein the highest amplitude and/or an average of the highest amplitude is displayed on the image.

* * * * *